United States Patent
Titus et al.

[11] Patent Number: 5,308,505
[45] Date of Patent: May 3, 1994

[54] METHOD FOR KILLING BARNACLE LARVAE IN WATER

[75] Inventors: James M. Titus, East Lyme; Bernard S. Ryskiewich, Pawcatuck, both of Conn.

[73] Assignee: General Dynamics Corporation, Falls Church, Va.

[21] Appl. No.: 972,236

[22] Filed: Nov. 5, 1992

Related U.S. Application Data

[62] Division of Ser. No. 773,102, Oct. 8, 1991.

[51] Int. Cl.⁵ .................................................. C02F 1/32
[52] U.S. Cl. .................................. 210/745; 210/748; 210/764; 422/6; 422/24
[58] Field of Search ............... 210/748, 747, 764, 243, 210/241, 745; 250/492.1, 504 R, 522.1, 432 R, 436–438; 422/6, 24, 186.3

[56] References Cited

U.S. PATENT DOCUMENTS

| | | | |
|---|---|---|---|
| 3,672,823 | 6/1972 | Boucher | 210/748 |
| 3,924,139 | 12/1975 | Hirose et al. | 210/320 |
| 3,971,338 | 7/1976 | Alexson | 119/5 |
| 4,204,956 | 5/1980 | Flatow | 210/748 |
| 4,317,041 | 2/1982 | Schenck | 250/435 |
| 4,320,085 | 3/1982 | Takeguchi et al. | 422/24 |
| 4,400,270 | 8/1983 | Hillman | 210/754 |
| 4,525,278 | 6/1985 | Frost | 210/748 |
| 4,548,716 | 10/1985 | Boeve | 210/652 |
| 4,762,613 | 8/1988 | Snowball | 210/748 |

FOREIGN PATENT DOCUMENTS

| | | |
|---|---|---|
| 2168977 | of 1973 | France . |
| 62-042785 | 2/1987 | Japan . |
| 62-042786 | 2/1987 | Japan . |

Primary Examiner—Neil M. McCarthy
Attorney, Agent, or Firm—Brumbaugh, Graves, Donohue & Raymond

[57] ABSTRACT

Biofouling of underwater surfaces by marine organisms is prevented by irradiating the water with ultraviolet light and adjusting the intensity of the ultraviolet light so as to kill barnacle larvae to prevent their attachment to the underwater surface. The water is passed through a biocidal chamber having a source of ultraviolet light at an intensity of at least 4000 $\mu$watts/cm$^2$ and at a rate to provide a residence time of at least one minute on the biocidal chamber.

2 Claims, 8 Drawing Sheets

METHOD FOR KILLING BARNACLE LARVAE IN WATER

This application is a division of application Ser. No. 07/773,102, filed on Oct. 8, 1991.

BACKGROUND OF THE INVENTION

Marine biofouling is present in all oceans and at all depths. Its character and magnitude are a function of physical and biological factors. Basically, marine growth varies as a function of temperature, food and light intensity. The mechanisms of marine biofouling are known and can be divided into the following five phases: (1) adsorption of organic molecules by the fouling surface (2) attachment of bacteria to the fouling surface, partially facilitated by the absorbed organic molecules (3) growth of bacteria and colony formation (4) accumulation of additional organic material and film formation (microfouling) and finally, (5) the attachment and growth of larger organisms (macrofouling), by organisms such as barnacles, mussels, etc.

The detrimental effects of marine biofouling are well known and wide ranging Biofouling affects the performance and efficiency of ships, commercial boating and marine installations, and is a major problem for the marine industry today. The same is also true of commercial coastal facilities, such as water treatment plants, power generation plants, oil platforms, etc.

Therefore, many attempts have been made to control biofouling. Periodic cleaning was probably the first method of control attempted. Copper cladding had been used on earlier wooden ships.

More recently, new techniques such as the use of new toxic paints, and toxic plastic materials have been devised. In addition, toxic chemicals made from seawater, by electrolysis or by introduction into the water, to kill the organisms are also currently in use. However, none of these methods have been entirely effective for controlling biofouling problems.

Tri-butyl tin oxide (TBTO) and copper-base paint systems have been traditionally used on Navy ships as a marine anti-foulant. TBTO is an environmental and health hazard and its use has been restricted. The copper-base paint type systems presently in use still present somewhat of a health hazard. Both the TBTO and the copper-base paint type systems are only effective under limited conditions.

Chlorinator systems are presently in use in Navy ships, commercial ships and marine facilities. However, chlorinator systems are also toxic. These systems are effective for the problem of marine biofouling in intakes and heat exchangers. Nevertheless, fouling of intakes, sea chests, tanks, on optical windows and hydrophones has continued. New methods and systems are needed to reduce the marine fouling in Navy and commercial ships and in commercial facilities, especially for pipes and intakes, cooling towers, transducer surfaces, optical windows and external mechanisms.

Further, most of the prevention systems in use today are toxic to the environment New programs established by the U.S. government and commercial industries aimed at "zero emissions" into the environment of toxic waste, are being implemented. Eventually a major portion of the currently used biofouling techniques will have to be eliminated to preserve the nation's water resources, especially in the Great Lakes. It has been found that what was originally thought to be safe toxic levels for marine life are in fact not. For example, findings show that the tolerance to organochlorines is much lower in fish than in mice. Preliminary research indicates that fish may be 1000 times more susceptible to organochlorine poisoning than mice. With such recent environmental concerns, greater and greater limitations will be placed on the present biofouling prevention techniques.

Accordingly, an object of this invention is to provide a solution to biofouling which is non-polluting to both the outlying and local environments, and is simplistic and reliable in application to the biofouling problem. It is therefore proposed, in accordance with the present invention, to apply the use of ultraviolet light for the prevention of marine biofouling. The ultraviolet power needed to prevent the biofouling from starting even at phase 2, is minimal, and recent experimental work clearly shows that UV prevention methods work effectively. A method is described herein in which ultraviolet light can be used to control biofouling by preventing attachment of marine organisms, stunning the organisms and also by exterminating the organisms.

SUMMARY OF THE INVENTION

In accordance with the invention, underwater objects are irradiated with ultraviolet light for the prevention of marine biofouling. Optionally, fiber optics may be used to convey ultraviolet light from a source to the surface of the underwater object. More specifically, marine biofouling is avoided by irradiation of specific surfaces of underwater objects with ultraviolet light to prevent attachment of marine biofouling organisms to those surfaces, to stun the biofouling organisms prior to removal, or to exterminate the marine biofouling organisms at either those specific surfaces or over a defined volume.

In small areas, where prevention is preferable, like intake gratings, valves, sensors, and optical ports, only enough ultraviolet light energy need be applied to render the area unlivable for the bio-organisms. For large surface areas, such as lengths of pipes, where prevention techniques are not practical, a biocidal approach can be taken. In this capacity, higher energy ultraviolet light is periodically applied to the biofouled surface. This higher energy ultraviolet light kills the organisms while in early larval stages of development during which attachment takes place.

DESCRIPTION OF THE DRAWINGS

Various objects, features and attendant advantages of the present invention will be more fully appreciated from the following detailed description when considered in connection with the accompanying drawings wherein.

DESCRIPTION OF PREFERRED EMBODIMENTS

Figure 1:
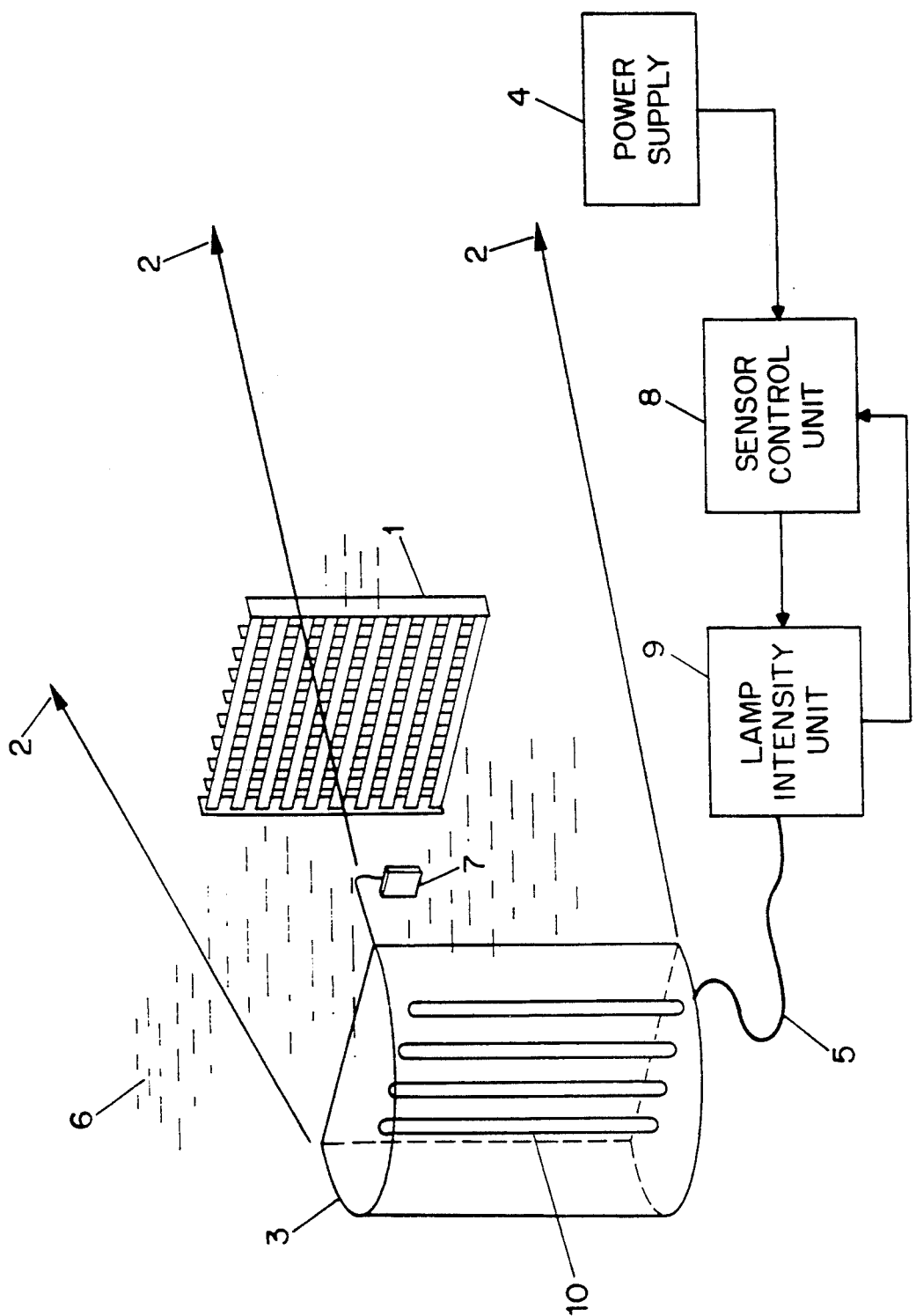
FIG. 1 is a diagrammatic perspective view illustrating a typical embodiment of an anti-fouling system in accordance with the invention.

In the representative embodiment of the invention shown in FIG. i, a stationary grating 1 which may be at one end of an intake or outlet pipe, and which is subject to biofouling, is irradiated by ultraviolet light rays 2 from an ultraviolet light assembly 3 designed for underwater operation. A power supply unit 4 provides the power necessary for starting and running a set of ultraviolet lamps 10 in the assembly 3 through an underwater cable which is capable of prolonged exposure to seawater. As the turbidity of the sea water 6 between the assembly 3 and the grating 1 changes, an ultraviolet sensor 7, for example an ultraviolet sensitive diode, detects the intensity changes, and provides corresponding signals through the cable 5 to a sensor control unit 8. The ultraviolet light intensity fluctuations are processed to provide a feedback signal to the lamp intensity unit 9. The intensity from the ultraviolet lamps 10 at the grating 1 is automatically adjusted in this way to maintain a minimum 20 $\mu$watt/cm$^2$ distribution over the irradiated area.

Preferably the underwater lamp assembly is capable of generating ultraviolet light having a wavelength of 250±10 nanometers and providing a minimum irradiation intensity of 20 $\mu$watt/cm$^2$ at a distance of at least two feet. Conventional ultraviolet light sources such as mercury, mercury/xenon, and xenon lamps have been found to provide satisfactory ultraviolet power output.

Figure 2:
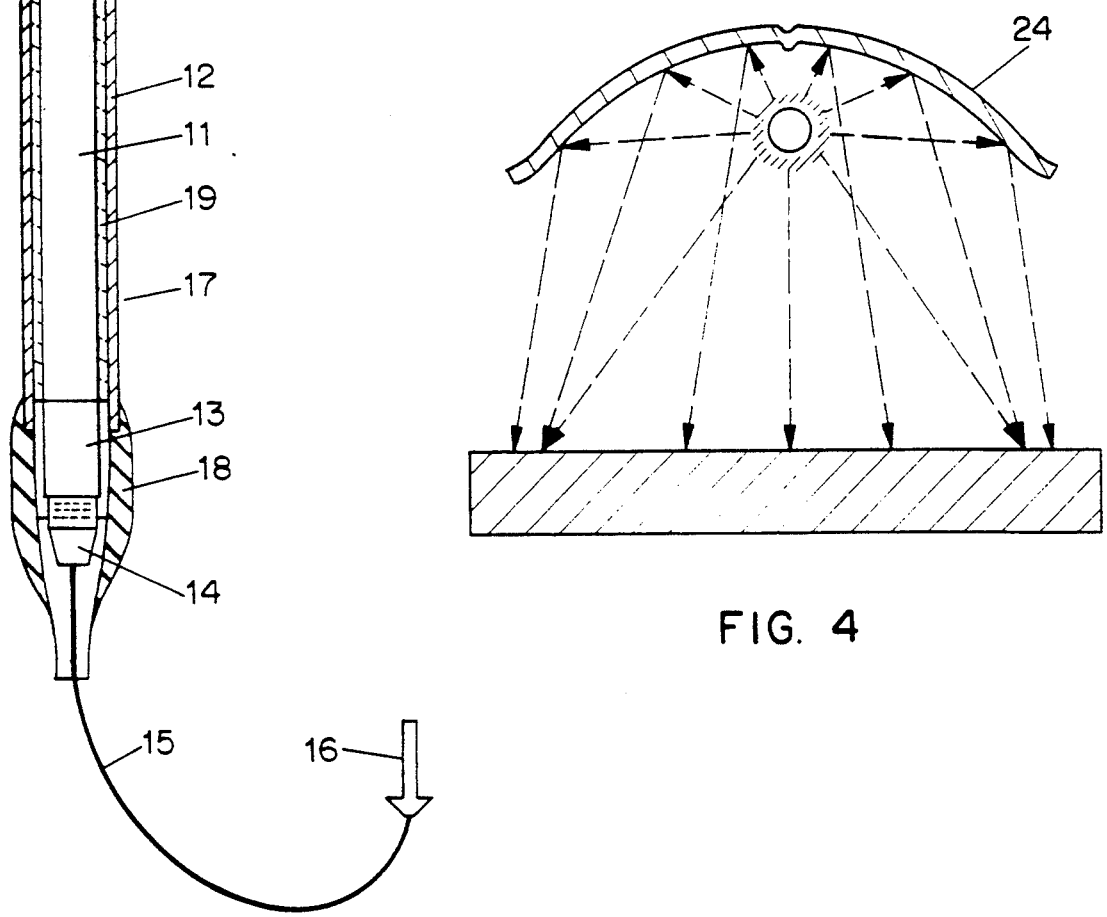
FIG. 2 is a longitudinal sectional view illustrating an ultraviolet light unit designed for use in accordance with the invention.

A typical underwater lamp unit 17 with a protective enclosure for facilitating continual underwater use is shown in FIG. 2. In this unit an ultraviolet lamp 11 is mounted in a tube 12 which is made from a material transparent to ultraviolet light such as quartz and closed at one end. The ultraviolet lamp is held in place by the O-rings 13 which are preferably made of an ultraviolet resistant material, for example, a fluorinated ethylene propylene copolymer. A connector 14 and a cable 15 are attached at one end of the lamp to supply power and a waterproof female connector 16 is provided at the other end of the cable. The connector is completely submersible and provides for quick installation and removal of the lamp unit while underwater. The lamp 11 is sealed from the environment by molding an ultraviolet resistant encapsulation material 18 around the open end of the tube 12 using a neoprene potting compound. The entire assembly is further protected from breakage by encapsulating the assembly in a ultraviolet transparent teflon sleeve 19.

Figure 3:
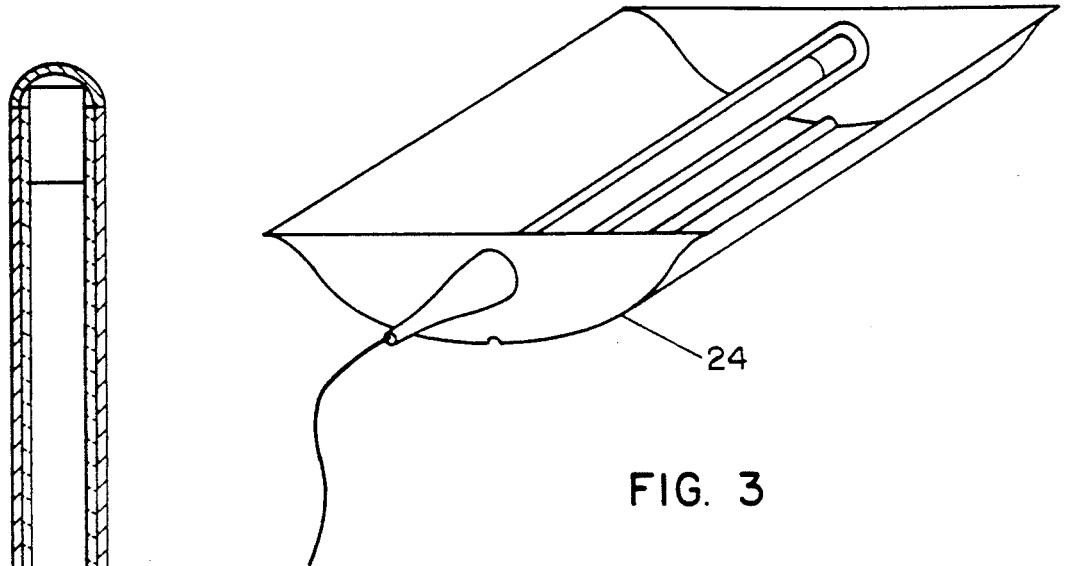
FIG. 3 is a perspective view showing the lamp of FIG. 2 mounted in a lamp reflector assembly in accordance with the invention.
Figure 4:
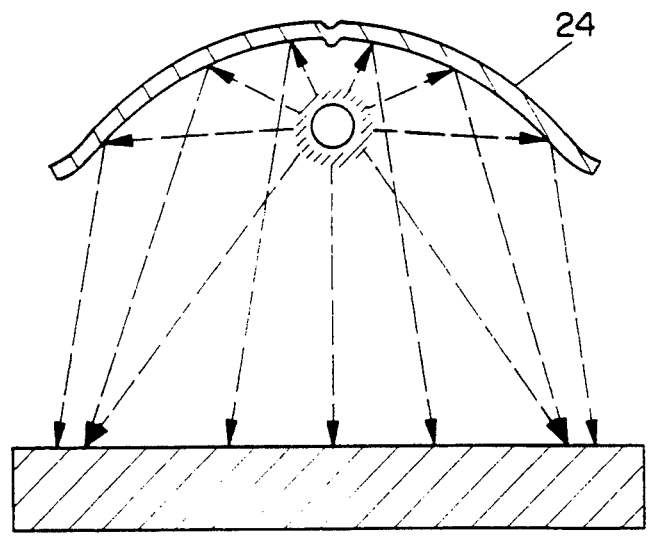
FIG. 4 is a schematic side view illustrating the distribution of ultraviolet radiation using the reflector assembly shown in FIG. 3.
Figure 5:
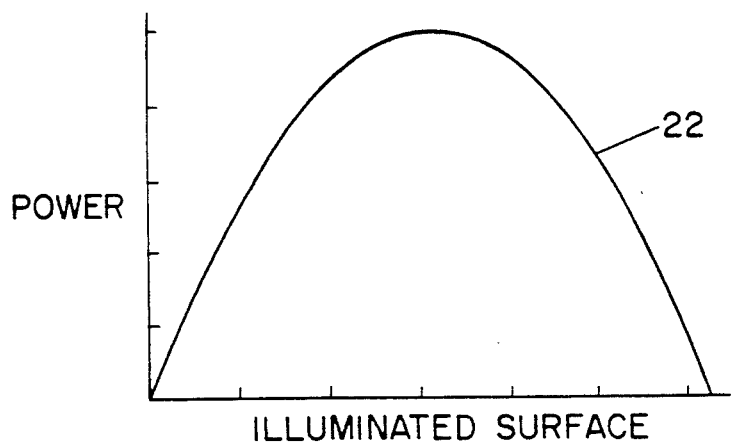
FIG. 5 is a graphical representation showing the distribution of ultraviolet light energy on an illuminated surface from the lamp of FIG. 2 in the absence of a reflector.
Figure 6:
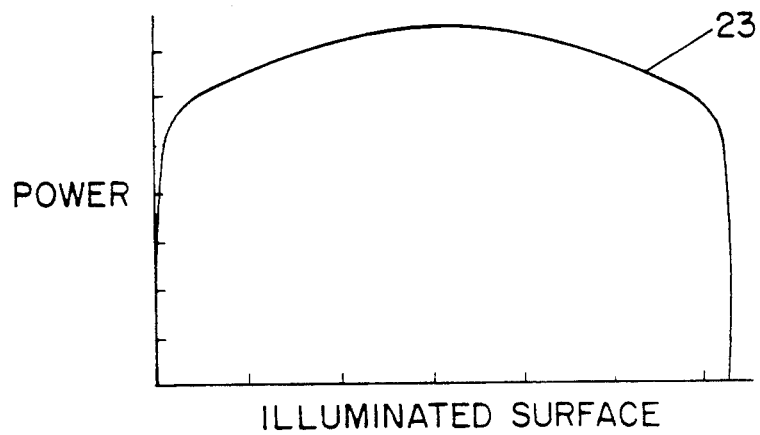
FIG. 6 is a graphical representation showing the distribution of ultraviolet light energy on an illuminated surface using the reflector assembly of FIG. 3.
Figure 7:
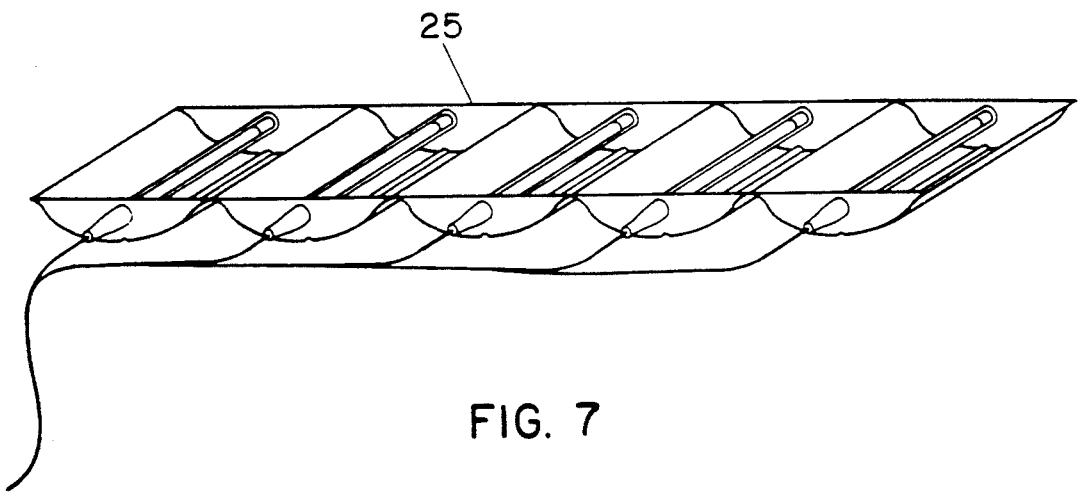
FIG. 7 is a perspective view showing an array of reflector assemblies for use in irradiating larger surface

In order to concentrate and direct the ultraviolet light energy across the underwater surface, a reflector housing 24 may be used in conjunction with the underwater lamp assembly as shown in FIGS. 3 and 4. The use of a reflector may be required for larger underwater surface areas where greater amounts of ultraviolet radiation are required. In the absence of a reflector, and excluding for light scattering due to turbidity effects, ultraviolet energy distribution is a function of cosine squared as shown by the curve 22 in FIG. 5. When a reflector 24 is used, the ultraviolet intensity distribution is a function of the shape of the reflector and the topography of the illuminated surface. A computer program utilizing a mathematical relation can be used to determine the optimum reflector shape. For a reflector having the proper shape, the light intensity is evenly distributed and there is an overall gain in intensity at the irradiated surface as illustrated by the curve 23 in FIG. 6. Suitable reflector materials include polished metals or metal alloys. Preferably, the reflector is made of polished aluminum coated with an optically transparent anti-corrosion material. Suitable coating include quartz and magnesium fluoride. The ultraviolet lamp assemblies are mounted in the reflector housing 24. When coverage of very large areas is required several reflector assemblies can be joined together in a radiation array 25 as shown in FIG. 7.

Figure 8:
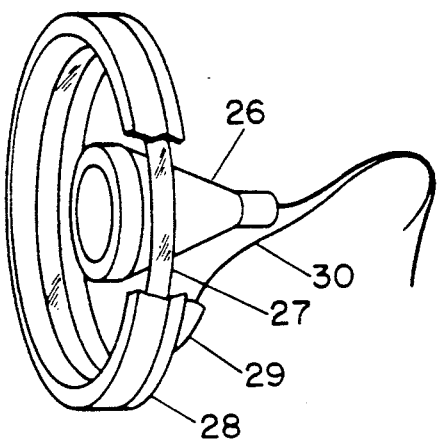
FIG. 8 is a perspective view showing an anti-fouling system for a ship sensor.

The marine antibiofouling system of the invention can be used to prevent attachment of biofouling organisms to underwater objects of any type. For example, FIG. 8 illustrates an embodiment in which an antifouling system is used in conjunction with an underwater sensor such as a hydrophone 26. In this case, a circular ultraviolet light source 27 is used so as to provide uniform illumination around the whole sensor and a reflector 28 surrounds the ultraviolet source to reflect radiation directed outwardly back toward the sensor. The assembly is sealed from the environment by ultraviolet resistant encapsulation material 29 and power cable 30 for the ultraviolet source is threaded along the hydrophone cable.

Figure 9:
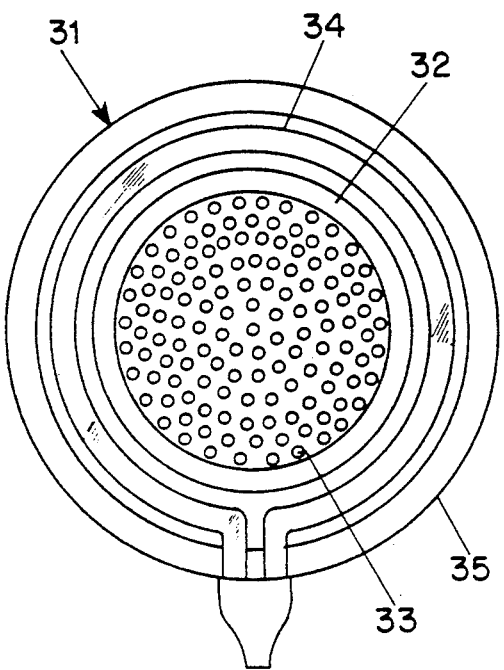
FIG. 9 illustrates an antifouling system for intake gratings.

FIG. 9 depicts an antibiofouling system for an underwater surface such as a grating. An anti-fouling system 31, installed at the intake surface of the grating 32, includes ultraviolet lamp 34 which illuminates the grating fully thereby keeping the grating intake holes 33 and the grating surface free of biofouling. Although a circular ultraviolet lamp 34 is shown, the lamp need not be circular. Factors considered in choosing the appropriate construction include the shape and size of the surface to be protected. A reflector 35 is provided to direct outwardly escaping ultraviolet radiation back toward the grating, thus optimizing the efficiency of the system.

Figure 10:
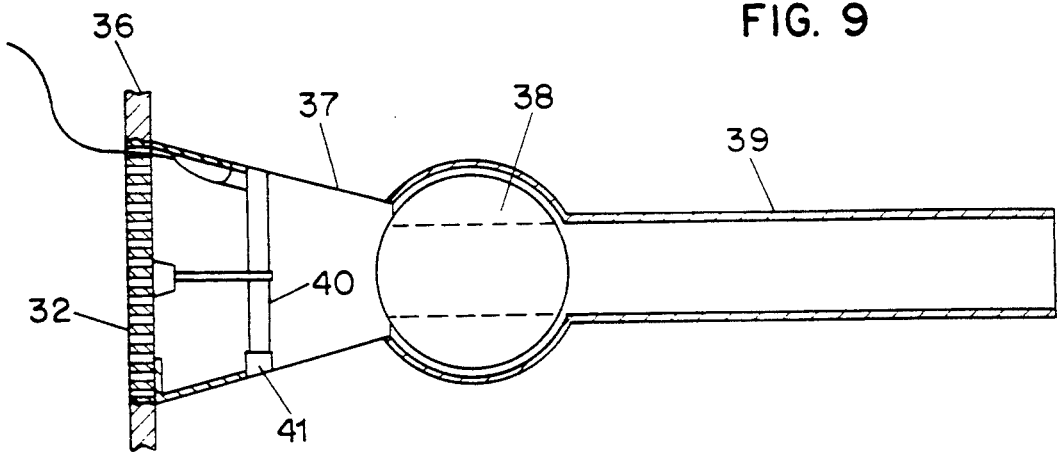
FIG. 10 shows the application of the invention to a valve.

FIG. 10 illustrates an arrangement for protecting a sea chest and valve structure 36. In this case, an antifouling system 40 is preferably placed inside the sea chest 37, between the intake grating 32 and a valve 38 leading to a pipe 39 affording maximum distribution of ultraviolet energy throughout the sea chest and the valve throat. In this manner, the major portion of the ultraviolet energy is concentrated within the sea chest while the scattered ultraviolet energy results in preventing biofouling through the entire assembly, even into the interior of the pipe 39. Preferably, the ultraviolet lamp 40 is mounted on the intake grating 32 and has an end 41 supported on the inside wall of the sea chest at an optimized location as shown in FIG. 10.

Figures 11, 12:
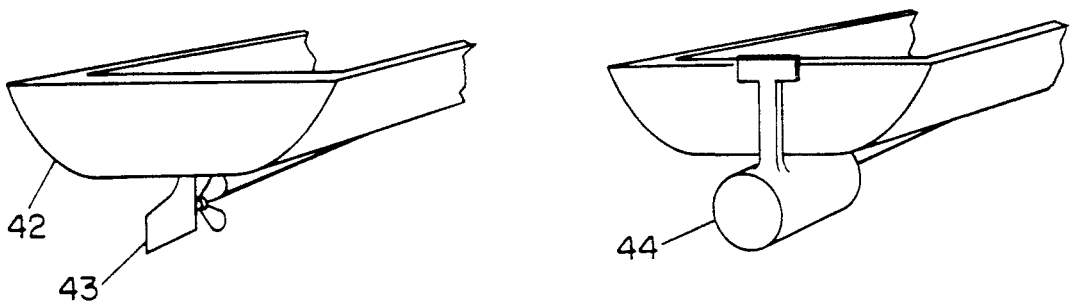
FIGS. 11 and 12 show the application of the invention to small commercial boats and pleasure craft.

FIGS. 11 and 12 show the use of an antibiofouling system with respect to a commercial boat or pleasure craft 42. A boat may be docked at a marina without use for a significant length of time, causing biofouling to develop in a region 43 which includes the rudder and propeller, as shown in FIG. 11, thus detracting from the performance of the boat. An antifouling system 44 arranged in accordance with this invention can be easily installed during idle periods to bathe the rudder and propeller area with the ultraviolet radiation as shown in FIG. 12, thus keeping these areas free of the performance-robbing biofouling. Preferably, the antifouling system is constructed of a plastic such as polyvinyl chloride (PVC) and contains an ultraviolet lamp similar in construction to those describe herein above. The system can be easily installed by suspending it from the boat's transom as shown in FIG. 12, where it will remain until the boat is used.

In an alternate embodiment, ultraviolet light is used as a biocide to locally kill biofouling organisms, thus preventing growth over a wide area. Typically, a specific surface or a defined volume of sea, river, or lake water is exposed to ultraviolet light for a finite length of time, thereby killing all the early developing larvae, and pre-empting the attachment and continued growth of the marine biofouling organisms. In the case of a specific surface, ultraviolet treatment is required only periodically because of time period for the transition from the swimming state to the settling stages of the marine organisms. In the case of a biocidal pool where volumes of sea, river, or lake water are treated continuous irradiation of the marine organisms is required. The result of this treatment in both cases is a reduced tendency for decaying animal debris to collect and contaminate the system after extermination.

Figure 13:
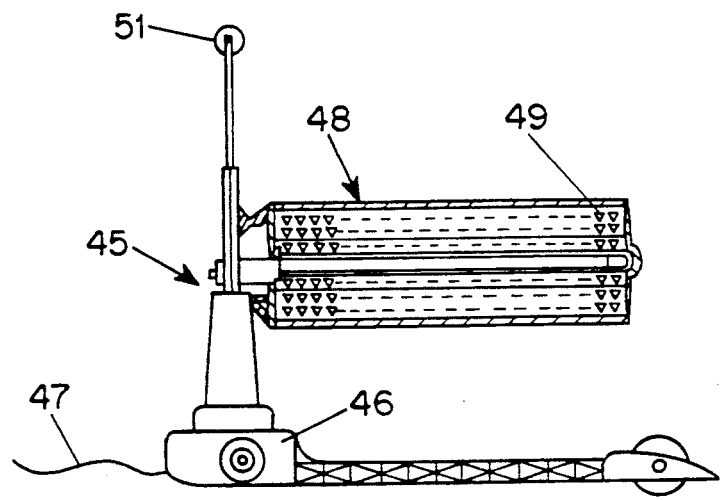
FIGS. 13-15 illustrate one form of an antifouling system according to the invention for use on intake piping.
Figure 14:
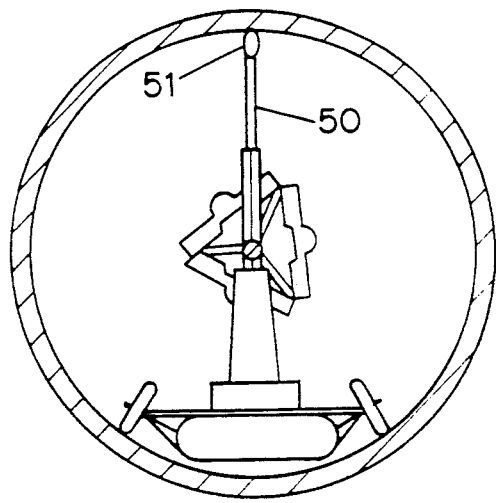
Figure 15:
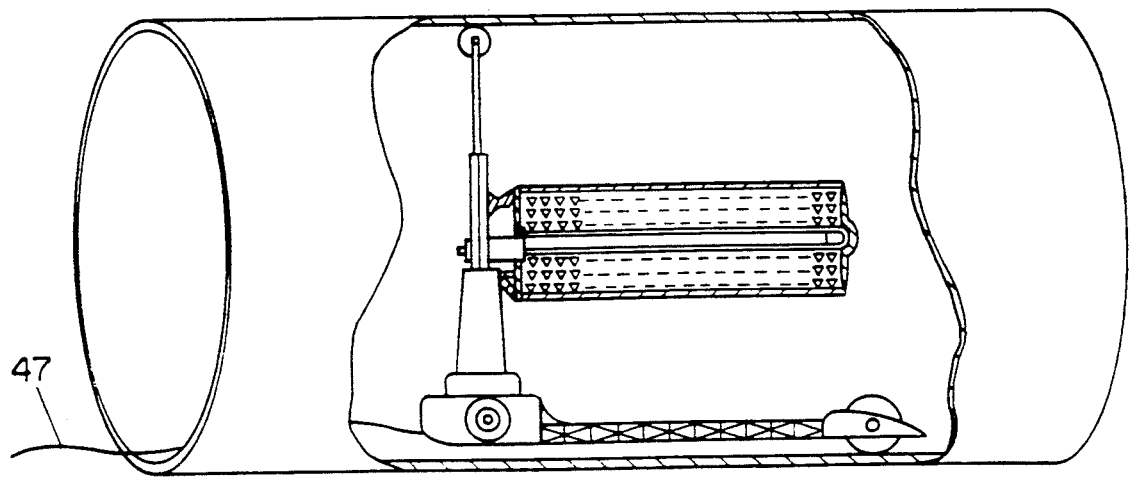

FIGS. 13-15 illustrate the application of the invention to intake pipes. Many industrial systems require that water be taken from or expelled into the environment through pipes, for cooling, water supply, irrigation, etc. Biofouling frequently occurs in these pipes, especially if the water in the pipes provides sufficient food and warmth for marine organisms to grow. FIG. 13 depicts a self-propelled device 45 which is designed to travel the length of small diameter pipes unattended, except for power needs. An electric motor drive 46 housed in the body of the device allows it to slowly traverse the length of the pipe. The device 45 supports an array 48 of ultraviolet irradiation lamps with reflectors 49 arranged to provide uniform irradiation throughout 360° to irradiate the entire interior surface of this pipe. Also housed within the body of the device is a microprocessor control system for monitoring the operations such as power requirements, time in standby mode, and fault identification, etc. The power and communication to the device is provided by a cable 47, extending from a tether and take-up reel system located at the entrance to the pipe. The speed of the device is a function of the ultraviolet intensity which is related to the length of the array 48, i.e. the longer the array, the greater the speed. Typically a two foot diameter pipe is equipped with an array two feet in length allowing, for example, a 300 foot pipe to be traversed in 2.5 hours. In this case the device 45 may have a total length of about 28 inches, for example.

The device 48 irradiates the entire length of the pipe with ultraviolet radiation, then once completed, goes into a standby mode until the next cycle. In the illustrated embodiment, three ultraviolet light units are provided in the device 48 as shown in FIG. 14 but the size and number of the units used in any particular case will depend on the diameter of the pipe. The device is constructed to support itself against the flows inside the pipe by continually adjusting to meet the curvature and discontinuities in the pipe. A tensioner system 50 shown in FIG. 14, is provided for support and adjustment to pipe discontinuities and a nose and front wheel assembly 51 acts as a guide in the pipe and a counter balance for the system. Preferably the device is designed to offer little restriction to the fluid flow profile area and the illustrated embodiment is only 13% of the cross section of the pipe.

The surface treatment rate is fixed by the development rate of the marine organisms. For example, if a pipe needs treatment once a week to keep the biofouling at a minimum then the life cycle of the device which is limited by ultraviolet lamp life, typically 7500 hours, is estimated to be 50 years, assuming no other system failures. Therefore, as designed, the antifouling system requires very little maintenance.

Figure 16:
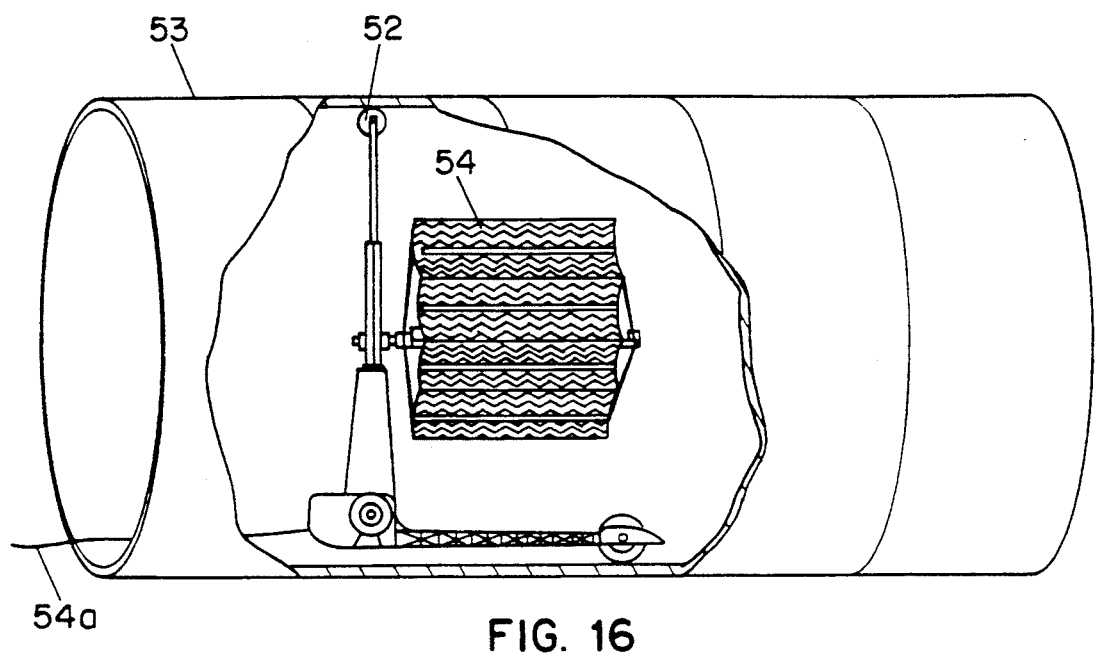
FIG. 16 is a perspective view, partly broken away, an anti-fouling system for very large diameter

FIG. 16 depicts an antifouling device similar to that of FIG. 13 for use in very large diameter pipes. In this device a much larger ultraviolet light array 54 is provided. The size of the array 54 is determined by the length of the pipe to be irradiated and by the diameter of the pipe. These factors determine the residence time of the antifouling system in the pipe which determines the traverse rate of the device itself. In the illustrated example the array 54 may be about seven feet long and the entire device may be about nine and one half feet long. Also, a tensioner system 52 not only provides support for the array but also adjusts the spacing of the array from the pipe wall, maintaining a uniform distance from the pipe surface to ensure sufficient coverage. FIG. 16 illustrates the device in a pipe 53 with a large array 54, that is rotated as the device moves through the pipe so that it progressively sweeps in corkscrew fashion over the inside the surface of the pipe until the entire inner-surface of the pipe is irradiated with the ultraviolet light. Power is provided by a cable 54a connected to a tether and take-up reel system, located at the pipe entrance. Since power requirements are minimal, as with the device illustrated in FIG. 14, the cable diameter is small in comparison to the device.

Figure 17:
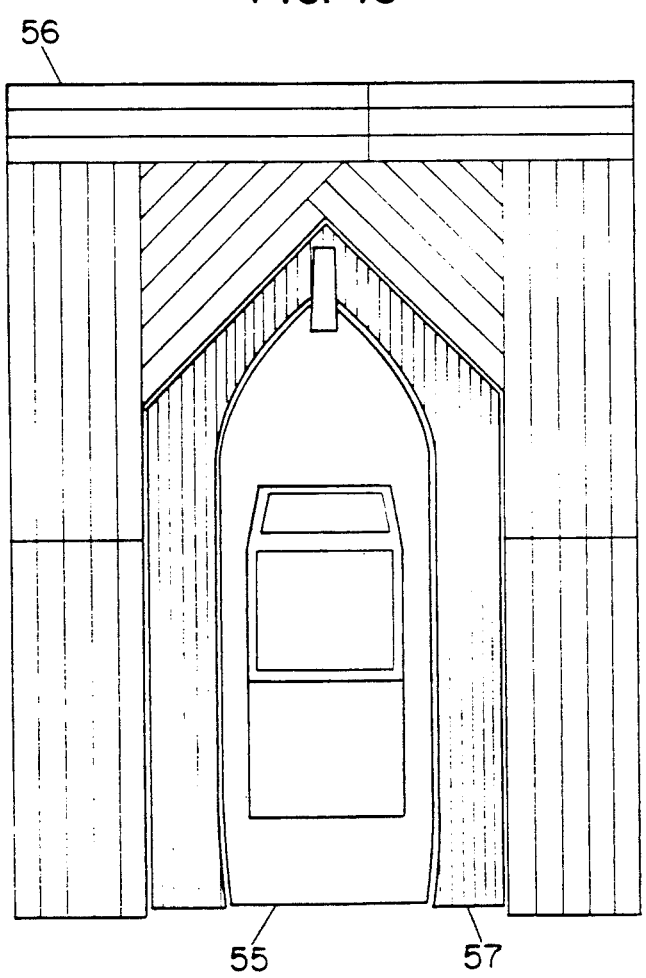
FIGS. 17 and 18 illustrate an anti-fouling system for use on boat hulls.
Figure 18:
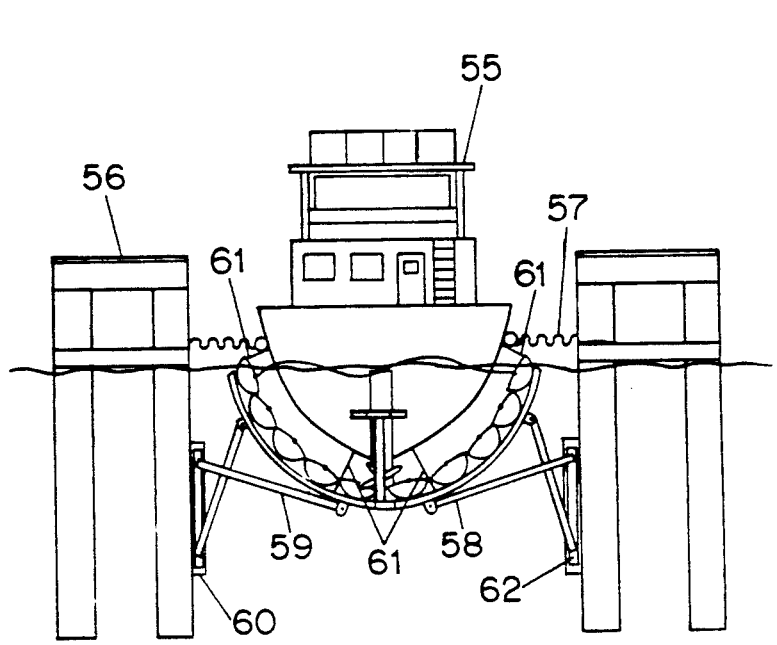

FIGS. 17 and 18 illustrate another biocidal antifouling application for the treatment of boat bottoms for the commercial boating industry. In this case a boat 55 is treated periodically to keep the hull free of marine growth during the boating season. For this purpose, the boat 55 is brought to a treatment area 56, a slip for example, designed to accept a variety of boats. A flexible opaque cover 57 is then extended out to the boat from the pier to keep the ultraviolet light which can be harmful to the human eye from escaping. An array of ultraviolet light/reflector assemblies 58, similar in construction to those shown in FIG. 3, are moved into position by a positioning mechanism 59 attached to a pier 60 near the boat's hull. Contact sensors 61 on the array determine the proper position of the array for application of the correct ultraviolet intensity to the hull. The array is then mechanically driven along a track 62 parallel to the hull, applying the ultraviolet light energy to the entire hull. Typically a five foot long array can be used to irradiated the hull of an average ocean pleasure boat in approximately 15 minutes.

Figure 20:
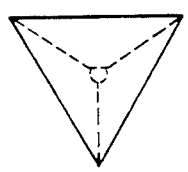
FIG. 20 is a side view of a support component used in the assembly of FIG. 19.
Figure 19:
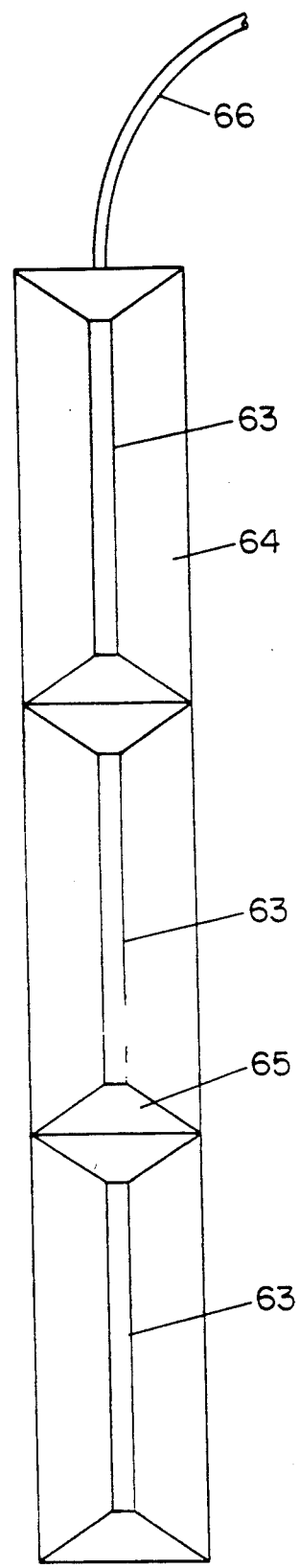
FIG. 19 is an elevational view of a high intensity emitter assembly for irradiating a surrounding water environment.

FIGS. 19-22 illustrate further examples of the invention. In these examples larva infested water is treated with ultraviolet light prior to entering intake pipes which provide cooling, water supply, irrigation, etc. Since the larvae are killed prior to the intake, the pipes and conduits stay clean automatically. FIGS. 19 and 20 illustrate a typical ultraviolet emitter which may be one of several stacked emitters, depending upon the application. As shown in FIG. 19 a space frame 64 holds a series of ultraviolet lamps 63 using spaced supports 65, one of which is illustrated in FIG. 20, and provides a conduit for a power line 66 leading to the lamps 63. Each individual lamp 63 is similar to that shown in FIG. 2, and each is individually removable from the frame. Depending upon the application, the emitter assembly may be as long as seven or eight feet, in the case of a central power plant, for example. The assembly irradiates the surrounding outer environment flowing transversely adjacent to it.

Figure 21:
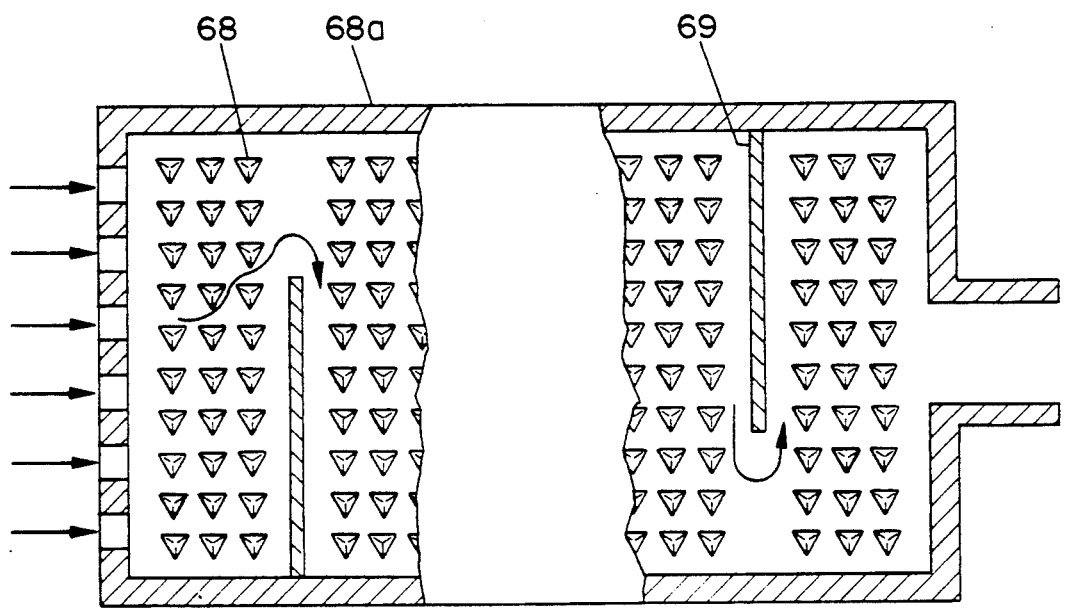
FIGS. 21 and 22 are plan and elevational views respectively of a biocidal chamber which may be used to kill or stun biofouling larvae as they pass through the chamber.
Figure 22:
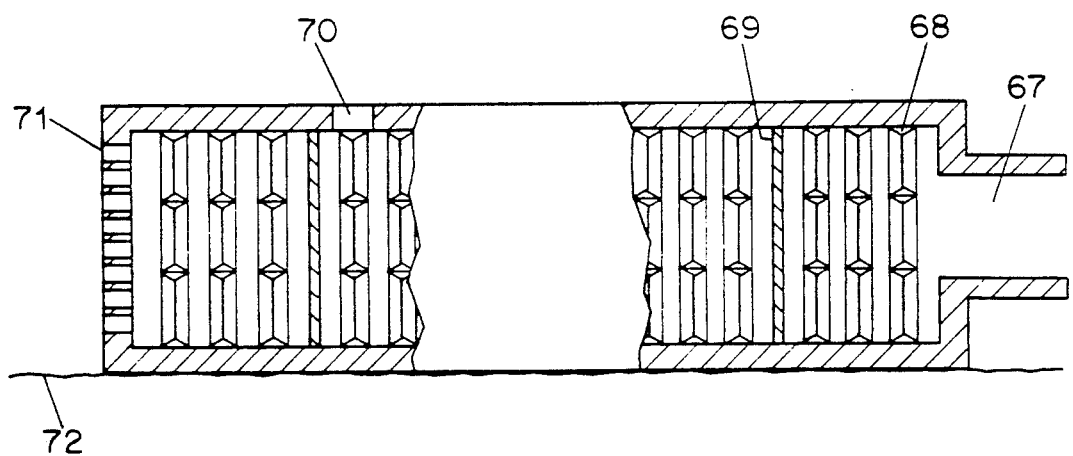

FIGS. 21 and 22 show an assembly containing an array of emitters 68 positioned in a biocidal chamber 68a to irradiate larva-infested water as the water flows through the chambers. Baffles 69 are positioned within the chamber to increase the residence time of the water within the chamber. Typically, in this type of arrangement all barnacle larvae are killed at a minimum irradiation intensity of 4000 $\mu$watt/cm$^2$ and a residence time of one minute or more. The chamber 68a has a simple rectangular shape and is of a size to provide the one minute residence time at reasonable flow rates. It can be positioned on the bed 72 of the ocean or a lake as shown in FIG. 22, or on land to receive water through an intake pipe 67. The walls and floor of the chamber 68a should be sufficiently strong to withstand applied appropriate pressures. The ceiling of the chamber can be a fixed ceiling with one or more manholes 70 for maintenance entry and egress as shown in FIG. 22, or a fixed ceiling with openings permitting removal of individual emitter assemblies for maintenance. If the chamber 68a is immersed in a body of water, the water may enter and leave at either of the extreme ends of the chamber. At the open end 71, single or multiple holes may be provided. Multiple holes are preferred in order to achieve a uniform flow distribution. The treated water, now free of biofouling larvae, leaves the chamber in single or multiple outlets depending upon the application.

In an alternate embodiment the larvae are stunned rather than killed. In this embodiment sufficient ultraviolet radiation is applied over a finite time period to render the larvae temporarily "dormant" so they will not attach to surfaces during their residence in the pipe, conduit, or system. This embodiment provides no ecological impact to the environment as the larva revive after removal and continue their normal life.

Although the invention has been described herein with reference to specific embodiments, many modifications and variations therein will readily occur to those skilled in the art. Accordingly, all such variations are included within the intended scope of the invention.

We claim:

1. A method for prevention of marine biofouling comprising the steps of:
   providing a biocidal chamber having a source of ultraviolet light;
   passing water containing barnacle larvae through the chamber;
   generating an ultraviolet light at an intensity of at least 4000 $\mu$watts/cm$^2$ within the chamber, and
   moving water through the chamber at a rate to provide a residence time of at least one minute wherein all barnacle larvae present in said water are killed by said ultraviolet radiation.

2. A method for prevention of marine biofouling comprising the steps of:
   providing a biocidal chamber having a source of ultraviolet light;
   passing water containing barnacle larvae through the chamber;
   automatically controlling the intensity of the ultraviolet light in response to a feedback signal so as to generate an ultraviolet light at an intensity of at least 4000 $\mu$watts/cm$^2$ within the chamber, and
   moving water through the chamber at a rate to provide a residence time of at least one minute wherein all barnacle larvae present in said water are killed by said ultraviolet radiation.

* * * * *